US011931228B2

United States Patent
Toscani et al.

(10) Patent No.: US 11,931,228 B2
(45) Date of Patent: Mar. 19, 2024

(54) APPARATUS AND METHOD FOR FORMING AN ABSORBENT PAD

(71) Applicant: GDM S.p.A., Bologna (IT)

(72) Inventors: Federico Toscani, Castelleone (IT); Matteo Piantoni, Albino (IT); Andrea Duchini, Castelleone (IT); Marco Rosani, Vailarate (IT)

(73) Assignee: GDM S.P.A., Bologna (IT)

( * ) Notice: Subject to any disclaimer, the term of this patent is extended or adjusted under 35 U.S.C. 154(b) by 810 days.

(21) Appl. No.: 16/965,848

(22) PCT Filed: Jan. 17, 2019

(86) PCT No.: PCT/IB2019/050379
§ 371 (c)(1),
(2) Date: Jul. 29, 2020

(87) PCT Pub. No.: WO2019/150211
PCT Pub. Date: Aug. 8, 2019

(65) Prior Publication Data
US 2021/0038441 A1     Feb. 11, 2021

(30) Foreign Application Priority Data
Jan. 30, 2018   (IT) .......................... 102018000002181

(51) Int. Cl.
*A61F 13/15*   (2006.01)
*B65H 37/04*   (2006.01)

(52) U.S. Cl.
CPC ....... *A61F 13/15634* (2013.01); *B65H 37/04* (2013.01); *A61F 2013/1591* (2013.01); *B65H 2301/5113* (2013.01); *B65H 2406/33* (2013.01)

(58) Field of Classification Search
CPC combination set(s) only.
See application file for complete search history.

(56) References Cited

U.S. PATENT DOCUMENTS 4,949,668 A * 8/1990 Heindel ................ B05C 5/0279
118/314
5,494,622 A * 2/1996 Heath ................ A61F 13/15658
425/81.1

(Continued)

FOREIGN PATENT DOCUMENTS

CN   105960224 A   9/2016
JP   2012152471 A   8/2012

(Continued)

OTHER PUBLICATIONS

Chinese Office Action dated Jun. 2, 2021 from counterpart Chinese Patent Application No. 201980010749.5.

(Continued)

*Primary Examiner* — Guy K Townsend
(74) *Attorney, Agent, or Firm* — SHUTTLEWORTH & INGERSOLL, PLC; Timothy J. Klima

(57) ABSTRACT

An apparatus for forming an absorbent pad for an absorbent sanitary article having a zone free of absorbent material to define a channel of the pad includes a forming drum, a first feed system for feeding a first web, a second feed system for feeding a second web, a spreader for spreading the absorbent material on the drum; a joining system for joining the first and second webs to define the channels. A first dispenser forms on the first web a layer of first adhesive substance according to a spreading pattern having zones free of the first adhesive substance corresponding to the channels. A second dispenser dispenses a second adhesive substance, whose adhesive force is greater than an adhesive force of the first adhesive substance, on the second web according to a pattern having a layer placed at a zone free of the first adhesive substance.

5 Claims, 3 Drawing Sheets

(56) References Cited

U.S. PATENT DOCUMENTS

| | | | | |
|---|---|---|---|---|
| 5,830,202 A * | 11/1998 | Bogdanski | A61F 13/5323 | 604/378 |
| 5,977,014 A * | 11/1999 | Plischke | A61F 13/535 | 604/378 |
| 6,641,695 B2 * | 11/2003 | Baker | A61F 13/15626 | 264/122 |
| 6,811,642 B2 * | 11/2004 | Ochi | A61F 13/15658 | 156/213 |
| 8,163,124 B2 * | 4/2012 | Moriura | A61F 13/5323 | 156/276 |
| 8,180,603 B2 * | 5/2012 | Blessing | B05C 19/04 | 703/2 |
| 8,183,431 B2 * | 5/2012 | Noda | A61F 13/536 | 604/380 |
| 8,206,533 B2 * | 6/2012 | Hundorf | A61F 13/15634 | 156/305 |
| 8,364,451 B2 * | 1/2013 | Blessing | A61F 13/15658 | 703/2 |
| 8,556,875 B2 * | 10/2013 | Takahashi | A61F 13/535 | 604/385.101 |
| 8,568,566 B2 * | 10/2013 | Jackels | D21F 11/08 | 118/244 |
| 8,663,182 B2 * | 3/2014 | Ashton | A61F 13/532 | 604/385.12 |
| 8,855,979 B2 * | 10/2014 | Blessing | B05C 1/0804 | 703/2 |
| 8,919,407 B2 * | 12/2014 | Hundorf | A61F 13/15634 | 156/383 |
| 9,044,359 B2 * | 6/2015 | Wciorka | A61F 13/536 | |
| 9,433,542 B2 * | 9/2016 | Kato | A61F 13/4756 | |
| 9,492,328 B2 * | 11/2016 | Jackels | D21F 11/08 | |
| 9,572,728 B2 * | 2/2017 | Ashton | A61F 13/532 | |
| 9,603,750 B2 * | 3/2017 | Van De Maele | A61F 13/15585 | |
| 9,668,926 B2 * | 6/2017 | Jackels | A61F 13/15764 | |
| 9,849,040 B2 * | 12/2017 | Hundorf | A61F 13/15699 | |
| 10,239,284 B2 * | 3/2019 | Schmitz | B29C 65/087 | |
| 10,245,188 B2 * | 4/2019 | Jackels | A61F 13/15658 | |
| 10,434,018 B2 * | 10/2019 | Wciorka | A61F 13/536 | |
| 10,555,840 B2 * | 2/2020 | Hundorf | B32B 5/30 | |
| 10,772,769 B2 * | 9/2020 | Van De Maele | A61F 13/15658 | |
| 10,786,400 B2 * | 9/2020 | Hashino | A61F 13/5121 | |
| 10,813,794 B2 * | 10/2020 | Jackels | B29C 59/022 | |
| 10,932,961 B2 * | 3/2021 | Goda | A61F 13/533 | |
| 11,000,422 B2 * | 5/2021 | Jackels | A61F 13/4704 | |
| 11,020,280 B2 * | 6/2021 | Van De Maele | B32B 37/24 | |
| 11,083,644 B2 * | 8/2021 | Wciorka | A61F 13/536 | |
| 11,083,645 B2 * | 8/2021 | Wciorka | A61F 13/496 | |
| 11,273,083 B2 * | 3/2022 | Bewick-Sonntag | A61F 13/51104 | |
| 11,759,372 B2 * | 9/2023 | Van De Maele | B32B 37/0076 | 428/206 |
| 2002/0056516 A1 * | 5/2002 | Ochi | A61F 13/15634 | 156/324 |
| 2002/0115969 A1 * | 8/2002 | Maeda | B01J 20/28026 | 604/368 |
| 2003/0144641 A1 * | 7/2003 | Chen | A61F 13/535 | 604/378 |
| 2003/0150551 A1 * | 8/2003 | Baker | A61F 13/15723 | 156/519 |
| 2006/0048880 A1 * | 3/2006 | Blessing | A61F 13/15634 | 156/367 |
| 2006/0278335 A1 * | 12/2006 | Moriura | A61F 13/5323 | 156/279 |
| 2007/0179469 A1 * | 8/2007 | Takahashi | A61F 13/535 | 604/385.101 |
| 2007/0299416 A1 * | 12/2007 | Noda | A61F 13/536 | 604/367 |
| 2008/0215166 A1 * | 9/2008 | Blessing | B05C 19/04 | 700/31 |
| 2008/0312617 A1 * | 12/2008 | Hundorf | B32B 37/144 | 156/60 |
| 2009/0056867 A1 * | 3/2009 | Moriura | A61F 13/5323 | 156/543 |
| 2009/0270825 A1 * | 10/2009 | Wciorka | A61F 13/539 | 604/378 |
| 2010/0004614 A1 * | 1/2010 | Ashton | A61F 13/5323 | 427/2.3 |
| 2010/0051166 A1 * | 3/2010 | Hundorf | B32B 38/1858 | 156/387 |
| 2010/0305533 A1 * | 12/2010 | Ashton | A61F 13/49466 | 604/386 |
| 2010/0305537 A1 * | 12/2010 | Ashton | A61F 13/49001 | 156/60 |
| 2011/0041999 A1 * | 2/2011 | Hundorf | A61F 13/5323 | 156/276 |
| 2011/0268932 A1 * | 11/2011 | Catalan | A61L 15/20 | 442/79 |
| 2012/0203527 A1 * | 8/2012 | Blessing | B05C 1/0804 | 703/2 |
| 2012/0312491 A1 * | 12/2012 | Jackels | D21F 11/08 | 162/297 |
| 2012/0316046 A1 * | 12/2012 | Jackels | B29C 65/4815 | 493/374 |
| 2012/0325408 A1 * | 12/2012 | Hundorf | B32B 37/1207 | 156/387 |
| 2013/0226120 A1 * | 8/2013 | Van De Maele | B32B 29/005 | 428/206 |
| 2013/0345656 A1 * | 12/2013 | Kato | A61F 13/537 | 604/375 |
| 2014/0027066 A1 * | 1/2014 | Jackels | A61F 13/00987 | 156/538 |
| 2014/0039437 A1 * | 2/2014 | Van De Maele | B32B 5/26 | 156/379.8 |
| 2014/0324007 A1 * | 10/2014 | Hundorf | A61F 13/536 | 604/366 |
| 2014/0338822 A1 * | 11/2014 | Mukai | A61F 13/15707 | 156/196 |
| 2015/0075711 A1 * | 3/2015 | Hundorf | A61F 13/15658 | 156/276 |
| 2015/0164699 A1 * | 6/2015 | Schmitz | B29C 66/83411 | 156/73.6 |
| 2015/0174857 A1 * | 6/2015 | Schmitz | B29C 65/087 | 156/146 |
| 2015/0230999 A1 * | 8/2015 | Wciorka | A61F 13/539 | 604/367 |
| 2016/0235606 A1 * | 8/2016 | Ashton | A61F 13/535 | |
| 2016/0331597 A1 * | 11/2016 | Piantoni | A61F 13/15764 | |
| 2017/0095377 A1 * | 4/2017 | Jackels | A61F 13/15642 | |
| 2017/0172810 A1 * | 6/2017 | Van De Maele | B05C 1/10 | |
| 2017/0231828 A1 * | 8/2017 | Jackels | A61F 13/15747 | 156/578 |
| 2018/0049924 A1 * | 2/2018 | Van De Maele | A61F 13/5323 | |
| 2018/0049925 A1 * | 2/2018 | Van De Maele | B05D 1/32 | |
| 2018/0064584 A1 * | 3/2018 | Van De Maele | B32B 3/28 | |
| 2018/0078426 A1 * | 3/2018 | Hundorf | A61F 13/5323 | |
| 2018/0098895 A1 * | 4/2018 | Hashino | A61F 13/5121 | |
| 2018/0228672 A1 * | 8/2018 | Wciorka | A61F 13/536 | |
| 2018/0228673 A1 * | 8/2018 | Wciorka | A61F 13/536 | |
| 2018/0228674 A1 * | 8/2018 | Wciorka | A61F 13/536 | |
| 2019/0038477 A1 * | 2/2019 | Jackels | A61F 13/15747 | |
| 2019/0038480 A1 * | 2/2019 | Goda | A61F 13/533 | |
| 2019/0133841 A1 * | 5/2019 | Bewick-Sonntag | A61F 13/51104 | |
| 2019/0183687 A9 * | 6/2019 | Van De Maele | B05C 1/10 | |
| 2019/0336361 A1 * | 11/2019 | Wciorka | A61F 13/495 | |
| 2020/0289336 A9 * | 9/2020 | Van De Maele | B32B 5/16 | |
| 2021/0038441 A1 * | 2/2021 | Toscani | B65H 37/04 | |
| 2021/0059875 A1 * | 3/2021 | Koyama | A61F 13/511 | |
| 2021/0259896 A1 * | 8/2021 | Wciorka | A61F 13/536 | |
| 2022/0015965 A1 * | 1/2022 | Wciorka | A61F 13/496 | |
| 2022/0023117 A1 * | 1/2022 | Wciorka | A61F 13/495 | |
| 2022/0142830 A1 * | 5/2022 | Lambertz | D04H 1/4291 | |
| 2022/0160550 A1 * | 5/2022 | Heege | A61F 13/536 | |
| 2022/0160551 A1 * | 5/2022 | Lambertz | A61L 15/225 | |
| 2022/0183905 A1 * | 6/2022 | Lambertz | D04H 1/54 | |
| 2023/0052286 A1 * | 2/2023 | Wciorka | A61F 13/536 | |

(56) References Cited

U.S. PATENT DOCUMENTS

| | | | |
|---|---|---|---|
| 2023/0081149 A1* | 3/2023 | Weber ................. | A61F 13/4756 156/243 |
| 2023/0240913 A1* | 8/2023 | Weber ............... | A61F 13/15658 604/378 |
| 2023/0248580 A1* | 8/2023 | Weber ............... | A61F 13/15658 604/378 |

FOREIGN PATENT DOCUMENTS

| WO | 0189439 A1 | 11/2001 |
|---|---|---|
| WO | 2017208500 A1 | 12/2017 |

OTHER PUBLICATIONS

English translation of Japanese Office Action dated Nov. 22, 2022 from counterpart Japanese Patent Application No. 2020-541496.
International Search Report and Written Opinion dated Mar. 13, 2019 from counterpart International Patent Application No. PCT/IB2019/050379.

* cited by examiner

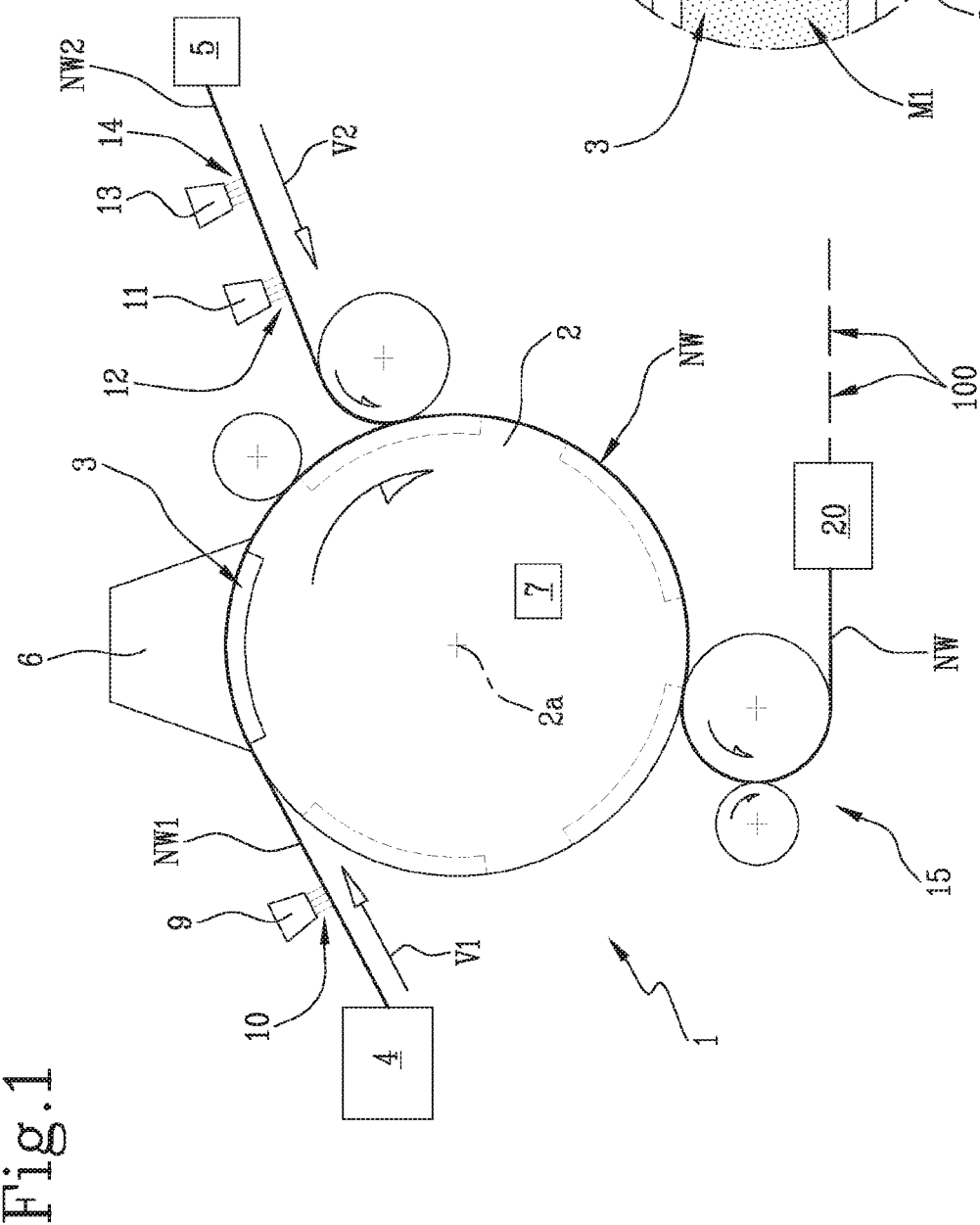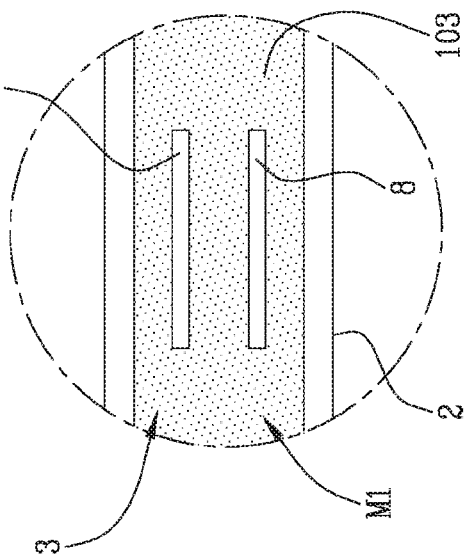
Fig.1
Fig.1A

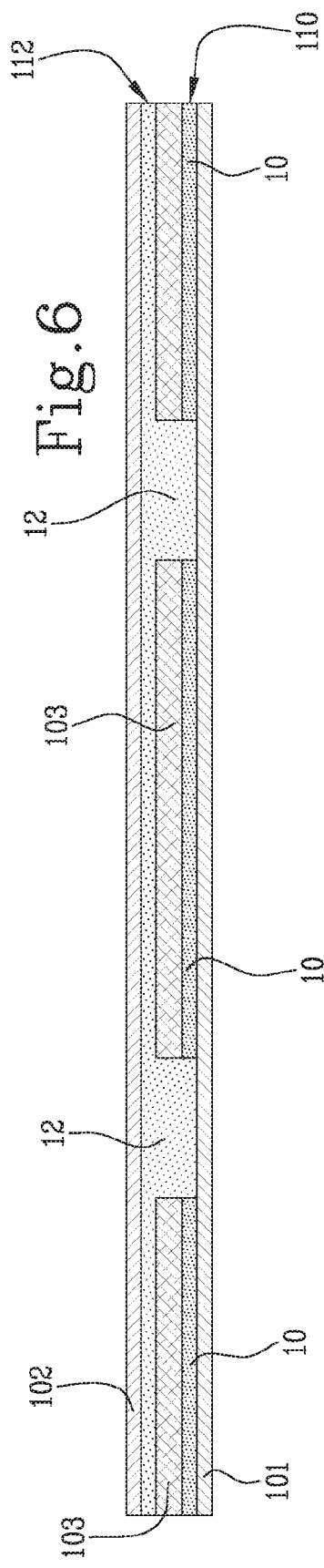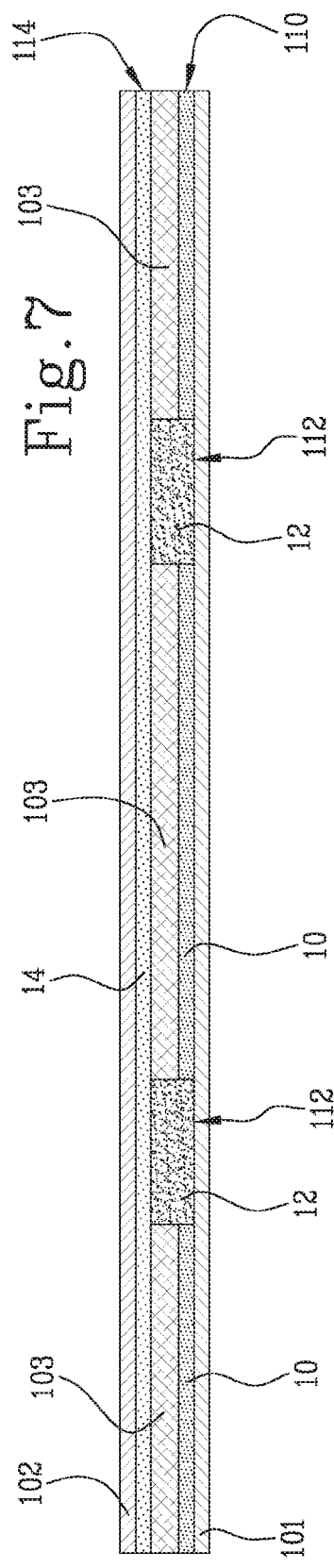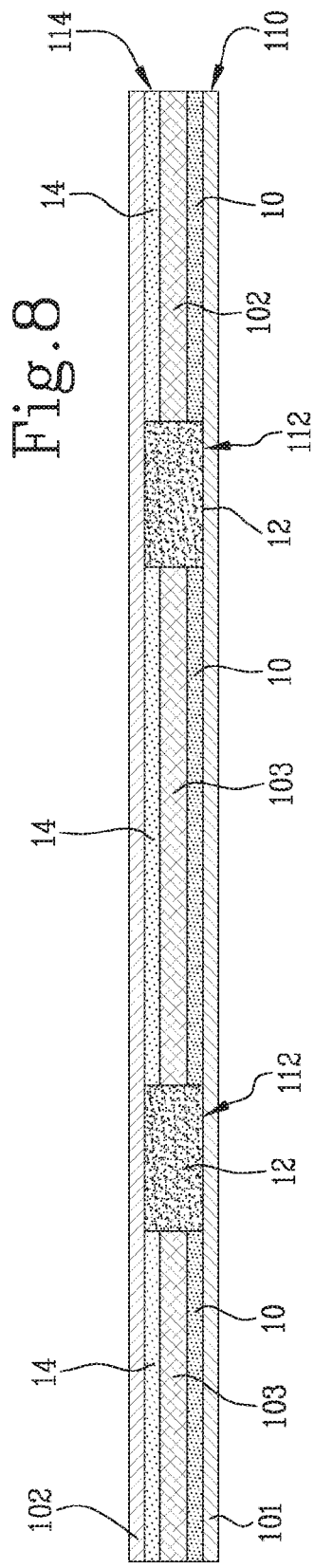

APPARATUS AND METHOD FOR FORMING AN ABSORBENT PAD

This application is the National Phase of International Application PCT/IB2019/050379 filed Jan. 17, 2019 which designated the U.S.

This application claims priority to Italian Patent Application No. 102018000002181 filed Jan. 30, 2018, which application is incorporated by reference herein.

TECHNICAL FIELD

This invention relates to an apparatus and a method for forming an absorbent pad or padding, also known in the trade as "core", intended for use in absorbent sanitary articles such as, for example, nappies for children and adults, to which express reference is hereinafter made without losing in generality, and the like.

BACKGROUND ART

As is known, nappies comprise an absorbent pad or padding whose absorbent core is generally made of beads of superabsorbent polymer material (SAP) inside a mixture of cellulose pulp (fluff), sandwiched between two layers of non-woven fabric.

To improve performance in terms of absorption, comfort and distribution of absorbed liquids, absorbent pads have been developed which are provided with longitudinal channels without absorbent material between the two layers of non-woven fabric.

In this context, known to the Applicant and competitors, for example from document EP2905001, are several solutions for apparatuses, and respective methods, for making absorbent padding provided with longitudinal channels that are free of absorbent material.

In this context, there is a need for developing and implementing a new and alternative solution for an apparatus, and a respective method, for making an absorbent pad of this kind.

AIM OF THE INVENTION

One aspect of this invention is to provide an apparatus for forming an absorbent pad for an absorbent sanitary article that comprises a first layer, a second layer and an absorbent material interposed between the first and the second layer.

The absorbent material is disposed according to a spreading pattern having at least one zone that is without, i.e. free of, the absorbent material and that is intended to define a respective channel in the pad.

The apparatus comprises a forming drum, a first feed system for feeding to the forming drum a first web, intended to form the first layer, and a second feed system for feeding to the forming drum a second web, intended to form the second layer.

The apparatus comprises at least one spreader for spreading the absorbent material on the forming drum, which comprises a suction system to create on the first web advancing on the forming drum, a spread of absorbent material according to the absorbent material spreading pattern.

The forming drum comprises at least one insert in the suction system. The insert defines a zone where suction is inhibited so that absorbent material is not retained and a channel is thus formed in the pad.

Placing the one or more inserts in a respective seat on the drum defines the pattern for spreading the absorbent material, where each zone that is free of absorbent material corresponds to the presence of an insert.

At least the first web, the second web and the absorbent material together form a composite web.

Downstream of the second feed system, the apparatus comprises a joining system for joining the composite web at least at the one or more zones which are free of absorbent material.

The apparatus comprises a first dispenser of a first adhesive substance on the first web located upstream of the spreader of the absorbent material with reference to the feed direction of the web itself.

The first dispenser is configured to create on the first web a layer of the first adhesive substance according to a spreading pattern having zones that are free of the first adhesive substance corresponding to the zones that are free of the absorbent material.

The apparatus comprises a second dispenser of a second adhesive substance on the second web, located upstream of the spreader of the absorbent material with reference to the feed direction of the web itself.

The second dispenser is configured to deliver the second adhesive substance on the second web according to a spreading pattern having at least one layer of the second adhesive substance intended to be spread at least at a respective zone that is free of the first adhesive substance.

Preferably, the adhesive force of the second adhesive substance is greater than the adhesive force of the first adhesive substance.

Advantageously, applying the second adhesive substance on the second web allows joining the first and the second web at the zone that is free of absorbent material and making on the padding a respective channel without absorbent material allows keeping the webs joined even when the absorbent material between the webs swells.

Advantageously, the use of the adhesive substance to join the first and the second web allows operating at high production speeds while keeping production costs low.

BRIEF DESCRIPTION OF THE DRAWINGS

Further features and advantages of this solution are more apparent in the non-limiting description below, with reference to a preferred but non-exclusive embodiment of an apparatus for forming a pad, as illustrated in the accompanying drawings, in which:

FIG. 1 is a schematic front view of an apparatus for forming an absorbent pad according to this invention;

FIG. 1a shows a scaled-up view of a detail from FIG. 1;

FIG. 6 shows a schematic transverse cross section of the pad of FIG. 5 having the spreading pattern of the second adhesive substance of FIG. 3;

FIGS. 7 and 8 show schematic transverse cross sections of the pad of FIG. 5 having the spreading pattern of the third adhesive substance combined with the spreading pattern of the second adhesive substance, in two variant embodiments.

DETAILED DESCRIPTION OF PREFERRED EMBODIMENTS OF THE INVENTION

Figure 2:
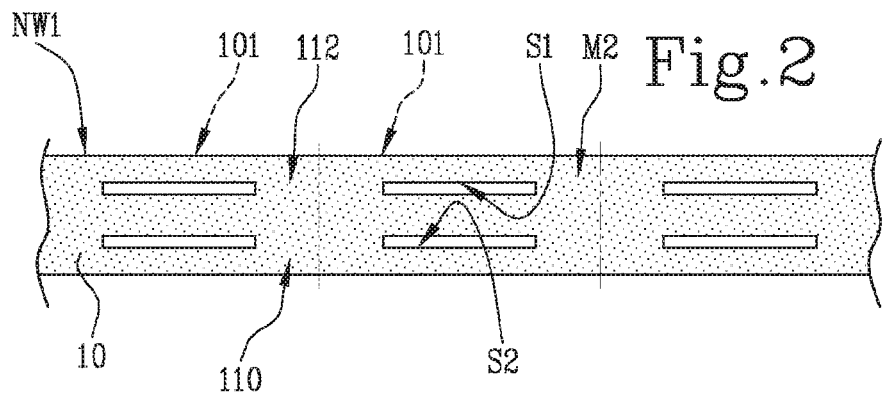
FIG. 2 shows a schematic top view of the spreading pattern of a first adhesive substance spread on a first web by a first spreader of the apparatus.

With reference to FIG. 1, the numeral 1 denotes an apparatus for forming absorbent pads 100 according to this invention.

This description of the apparatus 1 is limited to the parts necessary for understanding this invention.

The apparatus 1 comprises a drum 2 for forming the pads 100 and rotatable about an axis 2a.

Along its periphery, the drum 2 comprises a plurality of seats 3 for receiving the absorbent material 103.

In one embodiment, the seats 3 may be in the form of a single continuous circular seat 3 extending along a substantially cylindrical peripheral portion of the drum 2.

Alternatively, in another embodiment, of the type illustrated, the seats 3 are separate seats which are aligned and equispaced along a substantially cylindrical peripheral portion of the drum 2.

The shape of the seats 3 matches the shape of the pad 100.

A spreader 6 for spreading the absorbent material 103 is disposed on the forming drum 2 to confront at least part of the peripheral surface thereof in such a way as to allow filling the seats 3 which pass under the spreader 6 while the drum 2 rotates about its axis 2a.

The apparatus 1 comprises a first feed system, schematically represented as a block 4, for feeding a first web NW1 to the forming drum 2.

The web NW1 is intended to form a first layer 101 of the pad 100.

The web NW1 is movable in a feed direction V1 which is the same as the rotation direction of the drum 2.

The apparatus 1 comprises a second feed system, schematically represented as a block 5, for feeding a second web NW2 to the forming drum 2.

The second web NW2 is intended to form a second layer 102 of the pad 100.

The second web NW2 is movable in a feed direction V2 which is the same as the rotation direction of the drum 2.

The forming drum 2 comprises a suction system 7, schematically represented as a block, for drawing the absorbent material 103 into the receiving seat 3 of the drum 2.

The suction system 7 causes the first web NW1 to adhere to the peripheral surface of the drum 2, with reference to the location of the seats 3 for receiving the absorbent material 103.

Each seat 3 of the drum 2 is permeable to allow the suction of the drum 2 to retain the absorbent material 103 which settles on top of the first web NW1.

Thanks to the action of the suction system 7, each seat 3 is able to retain the absorbent material 103 while the drum 2 moves.

With reference in particular to the embodiment illustrated, it may be observed that each seat 3 of the forming drum 2 comprises at least one insert 8, or block 8, which prevents the absorbent material 103 from settling on it.

In the embodiment illustrated, each seat 3 of the forming drum 2 comprises at least a pair of inserts 8, or block 8.

The insert 8 extends in a longitudinal sense and in a transverse sense relative to the seat 3.

Each insert 8 is configured to define in the pad 100 a respective channel 104, 105 free of absorbent material 103.

The arrangement of the one or more inserts 8 in the seat 3 of the drum 2 defines a spreading pattern M1 for the absorbent material 103 having at least one zone Z1, Z2 free of absorbent material 103 at a respective insert 8 (see detail of FIG. 1).

The forming apparatus 1 comprises a first dispenser 9 of a first adhesive substance 10 on the first web NW1.

With reference to the feed direction V1, the first dispenser 9 is located upstream of the spreader 6 for spreading the absorbent material 103.

The first dispenser 9 is configured to create on the first web NW1 a layer 110 of the first adhesive substance 10 according to a spreading pattern M2 of the first adhesive substance 10.

The spreading pattern M2 of the first adhesive substance 10 corresponds to the pattern M1 for spreading the absorbent material 103: that is to say, the layer 110 of the first adhesive substance 10 is spread evenly and uninterruptedly on the web NW1 with zones S1, S2 which are free of the first adhesive substance 10 and which correspond to the zones Z1, Z2 free of the absorbent material 103.

Figure 5:
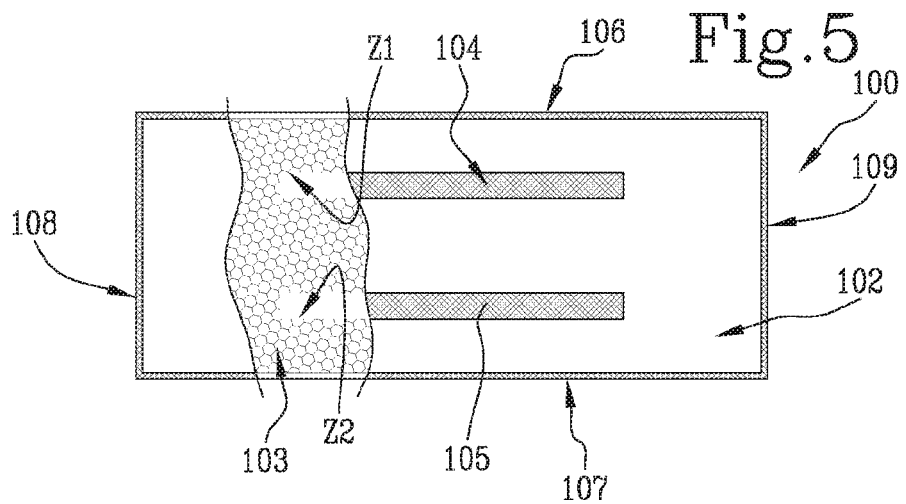
FIG. 5 shows an absorbent pad made by the apparatus of FIG. 1.

The zones S1, S2 free of the first adhesive substance 10 of the spreading pattern M2 for spreading the first adhesive substance 10 are intended to define the channels 104, 105 on the pad 100 (see FIG. 5).

The first adhesive substance 10 delivered by the first dispenser 9 is a substance whose adhesive force is such as to ensure that at least the absorbent material 103 is retained on the web NW1.

In particular, the first adhesive substance 10 delivered by the first dispenser 9 may also be known under the term "core integrity glue".

The apparatus 1 comprises a second dispenser 11 of a second adhesive substance 12 on the second web NW2.

With reference to the feed direction V2, the second dispenser 11 is located upstream of the drum 2.

The second dispenser 11 is configured to deliver the second adhesive substance 12 on the second web NW2 according to a spreading pattern M3 of the second adhesive substance 12.

Figure 3:
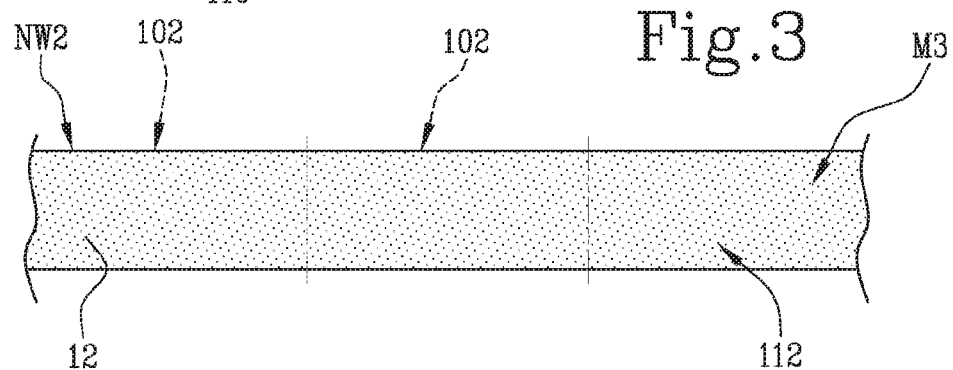
FIG. 3 shows a schematic top view of the spreading pattern of a second adhesive substance spread on a second web by a second spreader of the apparatus.
Figure 4:
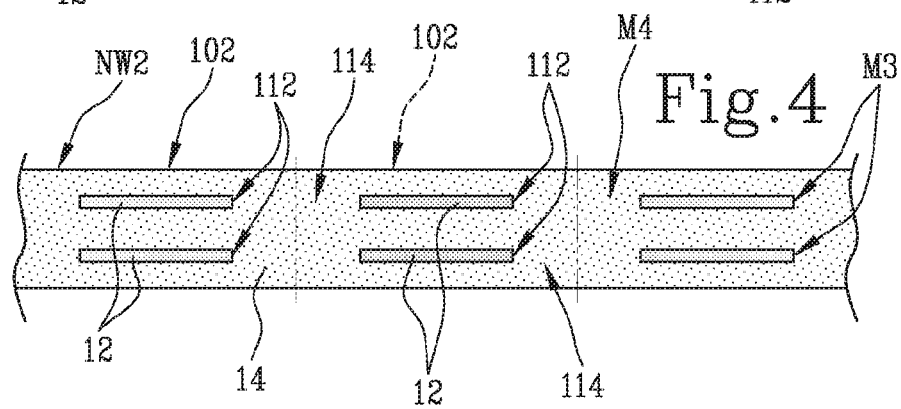
FIG. 4 shows a schematic top view of the spreading pattern of a third adhesive substance spread by a third spreader of the apparatus combined with the spreading pattern of the second adhesive substance, in a variant embodiment alternative to that of FIG. 3.

Generally speaking, the spreading pattern M3 of the second adhesive substance 12 comprises at least one layer 112 of the second adhesive substance 12 intended to be placed at least at a respective zone S1, S2 which is free of the adhesive substance 10 of the spreading pattern M2 (see FIGS. 3 and 4).

In a first variant embodiment, illustrated in FIG. 3, the spreading pattern M3 of the second adhesive substance 12 is a layer 112 spread evenly and uninterruptedly on the second web NW2.

By "evenly" is meant that the layer 112 of the second adhesive substance 12 is applied over the full width and length of the second web NW2.

By "uninterruptedly" is meant that the layer 112 of the second adhesive substance 12 is applied on the web NW2 without creating any zones which are free of the second adhesive substance 12.

It should be noted that in the variant of FIG. 3, the second adhesive substance 12 is spread also in the corresponding zones S1, S2 that are free of the first adhesive substance 10 of the spreading pattern M2.

In the variant embodiment of FIG. 4, the spreading pattern M3 of the second adhesive substance 12 has separate layers 112, each of which corresponds only to the respective zones S1, S2 free of the first adhesive substance 10 of the spreading pattern M2.

In this variant, the second dispenser 11 is preferably a sprayer.

Considering the variant of the spreading pattern M3 of FIG. 4, with one or more separate layers 112, the apparatus 1 comprises a third dispenser 13 of a third adhesive substance 14, located upstream of the second dispenser 16 in the feed direction V2 of the second web NW2.

The third dispenser 13 of a third adhesive substance 14 is an option for the variant embodiment.

The third dispenser 13 is configured to create on the second web NW2 a layer 114 of a third adhesive substance 14 according to a spreading pattern M4 of the third adhesive substance 14.

In a variant embodiment, in the spreading pattern M4 of the third adhesive substance 14, the layer 114 of the second adhesive substance 14 is spread evenly and uninterruptedly on the second web NW2.

By "evenly" is meant that the layer 114 of the third adhesive substance 14 is applied over the full width and length of the second web NW2.

By "uninterruptedly" is meant that the layer 114 of the third adhesive substance 14 is applied on the web NW2 without creating any zones which are free of the third adhesive substance 14.

In a variant embodiment, the spreading pattern M4 of the third adhesive substance 14 corresponds to the spreading pattern M2 of the second adhesive substance 12.

In other words, the spreading pattern M4 of the third adhesive substance 14 corresponds to the spreading pattern M1 of the absorbent material 103: that is to say, the layer 114 of the third adhesive substance 14 has zones which are free of the third adhesive substance 14 corresponding to the zones Z1, Z2 that are free of the absorbent material 103.

FIG. 4 shows the second web NW2 on which the pattern M4 of the third adhesive substance 14 is spread and which is combined with the pattern M3 of the second adhesive substance 12.

The pattern M3 of the second adhesive substance 12 is applied after the pattern M4 of the third adhesive substance 14.

In the variant embodiment of FIG. 4, the spreading pattern M3 of the second adhesive substance 12 may, in addition to the separate layers 112 of the second adhesive substance 12 of FIG. 4, each corresponding to a respective zone S1, S2 free of the first adhesive substance 10 of the spreading pattern M2, have longitudinal layers and transverse layers intended to define perimeter edges joining the first and the second webs NW1, NW2.

With reference to the adhesive force of the adhesive substances, it should be remembered that if the pad 100 comprises only the first adhesive substance 10 and the second adhesive substance 12, applied according to the spreading pattern of FIGS. 2 and 3, the second adhesive substance 12 is a substance whose adhesive force is such as to ensure that the first and the second webs of non-woven fabric NW1 and NW2 are joined to each other.

In a preferred variant embodiment, the adhesive force of the second adhesive substance 12 is greater than the adhesive force of the first adhesive substance 10.

If the pad 100 comprises the first adhesive substance 10, the second adhesive substance 12 and the third adhesive substance 14, applied according to the spreading pattern of FIGS. 2 and 4, the second adhesive substance 12 is a substance whose adhesive force is such as to ensure that the first and second webs of non-woven fabric NW1 and NW2 are joined to each other.

In a preferred variant embodiment, the adhesive force of the second adhesive substance 12 is greater than the adhesive force of the first adhesive substance 10 and of the third adhesive substance 14.

Preferably, the third adhesive substance 14 and the first adhesive substance 10 have the same adhesive force.

The first web NW1, the second web NW2, the absorbent material 103 and the adhesive substance 10, 12, 14, interposed between the first web NW1 and the second web NW2, together form a composite web NW.

Downstream of the second feed system 5, the apparatus 1 comprises a joining system 15 for joining the composite web at least at the second adhesive substance 12 located at the zones Z1, Z2 free of absorbent material 103 to define the channels 104, 105 of the pad 100.

In the embodiment illustrated, the joining system 15 comprises a first and a second pressing roller 16, 17 between which the composite web NW passes.

If the spreading pattern M3 of the second adhesive substance 12 has the longitudinal layers and the transverse layers intended to define the perimeter edges joining the first and the second webs NW1, NW2, the joining system 15 is configured to join the first and the second webs NW1, NW2 at the longitudinal and transverse layers so as to define the first and the second longitudinal edge 106, 107 and the first and the second transverse edge 108, 109 of the pad 100.

Alternatively, the apparatus 1 comprises a welding system, not illustrated, configured to join the first and the second webs NW1, NW2 in such a way as to define the first and the second longitudinal edge 106, 107 and the first and the second transverse edge 108, 109 of the pad 100.

A cutting device, schematically represented as a block 20, divides the composite web NW into individual pads 100.

FIG. 5 shows the pad 100 made by the apparatus 1 and used to make absorbent sanitary articles such as, for example, nappies for children or adults, comprising the first layer 101, the second layer 102 and the absorbent material 103.

The pad 100 is obtained by cutting the composite web NW into separate pieces.

The first layer 101 is a separate piece of the first web NW1.

The second layer 102 is a separate piece of the second web NW2.

The first and second layers 101, 102 are made, for example, of non-woven fabric.

The absorbent material 103 comprises, for example, cellulose fibres and superabsorbent material, also called SAP, and is sandwiched between the first and the second layer 101, 102.

The absorbent material 103 is disposed inside the pad according to the spreading pattern M1.

In the example illustrated, the pattern M1, hence the pad 100, has two zones Z1 and Z2 which are free of absorbent material 103.

As may be inferred from the cross section of FIG. 6, showing the variant embodiment of the pad 100 comprising only the first adhesive substance 10 and the second adhesive substance 12, the first and second layers 101, 102 are joined directly to each other by the second adhesive substance 12 at the channels 104, 105.

In other words, at the channels 104, 105, the pad 100 comprises in sequence, from the bottom up: the first layer 101, a layer 112 of the second adhesive substance 12 and the second layer 102.

At a portion of the pad 100 outside the channels 104, 105, the pad 100 comprises in sequence, from the top down: the first layer 101, a layer 110 of the first adhesive substance 10, the absorbent material 103, a layer 112 of the second adhesive substance 12 and the second layer 102.

With reference to the variant in which the pad 100 comprises a layer 114 of the third adhesive substance 14 spread according to the pattern M4 evenly and uninterruptedly on the second layer 102, it should be noted that at the channels 104, 105, the pad 100 comprises in sequence, from the bottom up: the first layer 101, a layer 112 of the second adhesive substance 12, a layer 114 of the third adhesive substance 14 and the second layer 102 (see FIG. 7).

At a portion of the pad 100 outside the channels 104, 105, the pad 100 comprises in sequence, from the bottom up: the first layer 101, a layer 110 of the first adhesive substance 10, the absorbent material 103, a layer 114 of the third adhesive substance 14 and the second layer 102 (see FIG. 7).

With reference to the variant of the pattern M4 of the third adhesive substance 14 comprising the zones free of the third adhesive substance corresponding to the zones Z1, Z2 free of absorbent material 103, it may be inferred from FIG. 8 that at the channels 104, 105, the pad 100 comprises in sequence, from the bottom up: the first layer 101, a layer 112 of the second adhesive substance 12, and the second layer 102.

At a portion of the pad 100 outside the channels 104, 105, the pad 100 comprises in sequence, from the bottom up: the first layer 101, a layer 110 of the first adhesive substance 10, the absorbent material 103, a layer 114 of the third adhesive substance 14 and the second layer 102 (see FIG. 8).

Like the variant of FIG. 6, in the variant embodiment of FIG. 8, too, the first and second layers 101, 102 are joined directly to each other by the second adhesive substance 12.

Generally speaking, as may be inferred from the variants illustrated, the pad 100 has two channels 104, 105 where the first and the second layer 101 and 102 are joined directly to each other at least by the second adhesive substance 12.

In the preferred embodiment illustrated by way of example, the pad 100 has a first and a second longitudinal edge 106, 107 along which the first and second layers 101, 102 are joined directly to each other.

In the preferred embodiment illustrated by way of example, the pad 100 has a first and a second transverse edge 108, 109 along which the first and second layers 101, 102 are joined directly to each other.

Also an object of this invention is a method for forming the absorbent pad 100, comprises a step of feeding the first web NW1, intended to form the first layer 101 of the pad 100.

The method comprises a step of feeding a second web NW2, intended to form the second layer 102 of the pad 100.

The method comprises a step of spreading the absorbent material 103 on the first web NW1 according to the spreading pattern M1.

The method comprises a step of joining the first and second webs NW1, NW2 at the zones Z1, Z2 free of absorbent material 103 to define the channels 104, 105 of the pad 100.

The method comprises a step of spreading a layer 110 of he first adhesive substance 10 on the first web NW1 according to the spreading pattern M2 having zones S1, S2 free of the first adhesive substance 10 corresponding to the zones Z1, Z2 free of the absorbent material 103.

The method comprises a step of spreading the layer 112 of the second adhesive substance 12 on the second web NW2 according to the spreading pattern M3 having at least one layer 112 of the second adhesive substance 12 which is intended to be placed at least at a respective zone S1, S2 that is free of the first adhesive substance 10.

In the spreading pattern M3, there is one layer 112 of the second adhesive substance 12 spread evenly and uninterruptedly on the second web NW2 or there are one or more separate layers 112 of the second adhesive substance 12 corresponding to the respective zones S1, S2 free of the first adhesive substance 10 of the spreading pattern M2.

In the variant of FIG. 7, The method comprises a step of spreading a layer 114 of a third adhesive substance 14 on the second web NW2 according to a spreading pattern M4 having a layer 114 of the third adhesive substance 14 spread uniformly and uninterruptedly on the second web NW2.

Alternatively, the method comprises a step of spreading the layer 114 of the third adhesive substance 14 on the second web NW2 according to a spreading pattern M4 corresponding to the spreading pattern M2 of the first adhesive substance 10, as shown in FIG. 8.

The step of spreading the layer 114 of the third adhesive substance 14 on the second web NW2 according to the pattern M4 is carried out before the step of spreading the layer 112 of the second adhesive substance 12 on the second web NW2 according to the spreading pattern M3.

The method comprises a step of joining the first web NW1 to the second web NW2 at least at the layers 112 of the second adhesive substance 12 disposed at the zones Z1, Z2 free of absorbent material 103 to define the channels 104, 105 of the pad 100.

A step of spreading a layer 112 of a second adhesive substance 12 on the second web NW2 according to a spreading pattern M3 which, in addition to the layer 112 of the second adhesive substance 12 corresponding to a respective zone S1, S2 free of the first adhesive substance 10 of the spreading pattern M2, has longitudinal layers and transverse layers of the second adhesive substance 12 intended to define perimeter edges 106, 107, 108, 109 joining the first and the second webs NW1, NW2.

Generally speaking, the step of spreading the layer 114 of a third adhesive substance 14 on the second web NW2 according to a pattern M4 is carried out before the step of spreading a layer 112 of a second adhesive substance 12 on the second web NW2 according to a spreading pattern M3.

A step of joining the first and the second webs NW1, NW2 at the aforesaid layers in order to define the first and the second longitudinal edge 106, 107 and the first and the second transverse edge 108, 109 of the pad 100.

The invention claimed is:

1. An apparatus for forming an absorbent pad for an absorbent sanitary article, the pad comprising a first layer, a second layer and an absorbent material interposed between the first and the second layer and arranged according to an absorbent material spreading pattern having at least one zone free of absorbent material and configured to define a respective channel, the apparatus comprising: a forming drum having one or more forming pockets for forming the absorbent material,
   a first feed system for feeding a first web, configured to form the first layer of the pad, to the forming drum,
   a second feed system for feeding a second web, configured to form the second layer of the pad, to the forming drum,
   at least one spreader for spreading the absorbent material on the forming drum;
   a suction system to create on the first web disposed on the forming drum a spread of absorbent material according to the absorbent material spreading pattern;

the forming drum comprising at least one insert in the suction system to inhibit suction at the at least one insert so that absorbent material is not retained and defines a respective channel; the arrangement of the at least one insert in a respective one of the one or more forming pockets of the drum defining the absorbent material spreading pattern wherein each of the at least one zone free of absorbent material corresponds to a presence of a respective one of the at least one insert;

at least the first web, the second web and the absorbent material defining a composite web;

a joining system for joining the composite web, located downstream of the second feed system at least at the at least one zone free of absorbent material to define the respective channel of the absorbent pad, a first dispenser of a first adhesive substance on the first web located, with reference to the feed direction, upstream of the at least one spreader for spreading the absorbent material; the first dispenser being configured to create on the first web a layer of the first adhesive substance according to a second spreading pattern having zones free of the first adhesive substance corresponding to the at least one zone free of the absorbent material;

a second dispenser of a second adhesive substance on the second web located, with reference to the feed direction, upstream of the at least one spreader for spreading the absorbent material; the second dispenser being configured to deliver the second adhesive substance on the second web according to a third spreading pattern having one or more layers of the second adhesive substance at least at the respective zones free of the first adhesive substance of the second spreading pattern;

an adhesive force of the second adhesive substance being greater than an adhesive force of the first adhesive substance.

2. The apparatus according to claim 1, wherein the third spreading pattern has a layer of the second adhesive substance spread uniformly and uninterruptedly on the second web; the layer of the second adhesive substance being spread also in the corresponding zones free of the first adhesive substance of the second spreading pattern.

3. The apparatus according to claim 1, wherein the third spreading pattern has one or more discrete layers of the second adhesive substance corresponding only to the respective zones free of the first adhesive substance of the second spreading pattern.

4. The apparatus according to claim 1, and further comprising:

upstream of the second dispenser with reference to the feed direction of the second web, a third dispenser of a third adhesive substance according to a fourth spreading pattern having a layer of the third adhesive substances spread uniformly and uninterruptedly on the second web; the layer of the third adhesive substance being spread also in the corresponding zones free of the first adhesive substance of the second spreading pattern;

the adhesive force of the third adhesive substance being equal to the adhesive force of the first adhesive substance.

5. The apparatus according to claim 1, and further comprising:

upstream of the second dispenser with reference to the feed direction of the second web, a third dispenser of a third adhesive substance according to a fourth spreading pattern corresponding to the second spreading pattern of the first adhesive substance; the fourth spreading pattern of the third adhesive substance having zones free of the third adhesive substance corresponding to the zones free of the absorbent material; the layer of the second adhesive substance corresponding to a respective zone free of the first adhesive substance of the second spreading pattern and a respective zone free of the third adhesive substance;

the adhesive force of the third adhesive substance being equal to the adhesive force of the first adhesive substance.

* * * * *